United States Patent [19]

Bauer et al.

[11] 4,380,176

[45] Apr. 19, 1983

[54] ISOBAROMETRIC AND SELF-CONTAINED APPARATUS FOR SAMPLING PURPOSE ON GASEOUS DRINKS

[75] Inventors: Gilbert Bauer, Mutzig; Michel Maurer, Strasbourg, both of France

[73] Assignee: Brasseries Kronenbourg, Strasbourg, France

[21] Appl. No.: 231,511

[22] Filed: Feb. 4, 1981

[30] Foreign Application Priority Data

Feb. 5, 1980 [FR] France .............................. 80 02743

[51] Int. Cl.³ .............................................. G01N 1/10
[52] U.S. Cl. ............................... 73/863.86; 73/864.61
[58] Field of Search ........... 73/863.81, 863.86, 864.61; 141/14, 39

[56] References Cited

U.S. PATENT DOCUMENTS

| | | | |
|---|---|---|---|
| 988,657 | 4/1911 | Pfaff | 141/39 |
| 3,010,583 | 11/1961 | Kenyon | 73/864.61 |
| 4,213,342 | 7/1980 | Gates | 73/864.61 |

FOREIGN PATENT DOCUMENTS

| | | |
|---|---|---|
| 2187115 | 1/1974 | France . |
| 2379816 | 9/1978 | France . |
| 2410824 | 6/1979 | France . |

*Primary Examiner*—S. Clement Swisher
*Attorney, Agent, or Firm*—Benoit Law Corporation

[57] ABSTRACT

The invention relates to a self-contained apparatus used for constant pressure sampling of gaseous beverages especially during fermentation.

The apparatus is provided with a tripod (3) and grip frame (15) with a stand for the sampling container (20) and for an inert gas bottle.

In the upper part, a distribution-head has two inlet-taps (23 and 24), a pressure-tap (35), and a closing member with an injection cannula (21).

Moreover, the apparatus comprises between the distribution-head (16) and the pressure-tap (35) an element (38) for adjusting the flow of the evacuating system, being operated by the pressure-tap.

11 Claims, 7 Drawing Figures

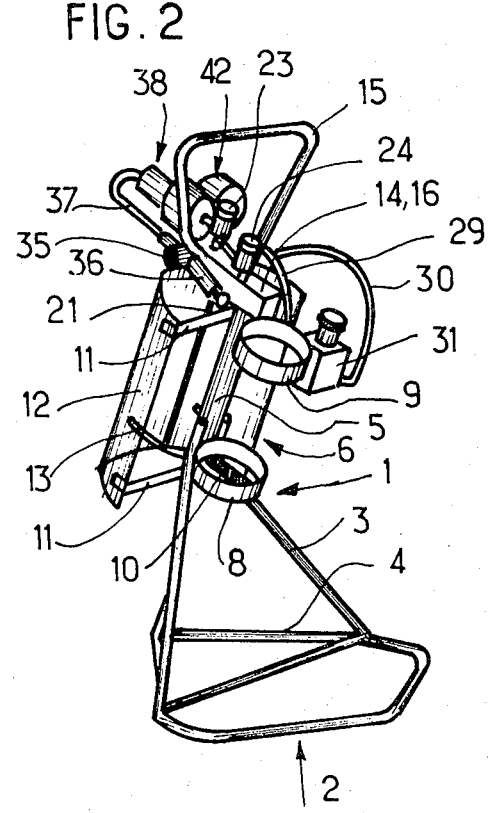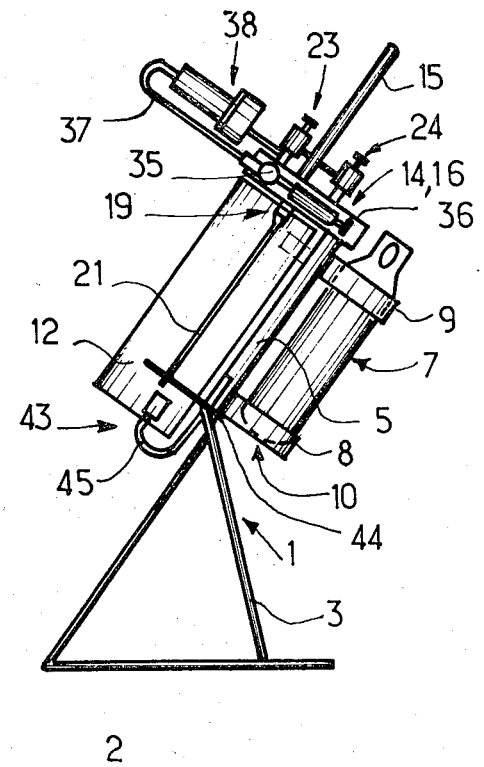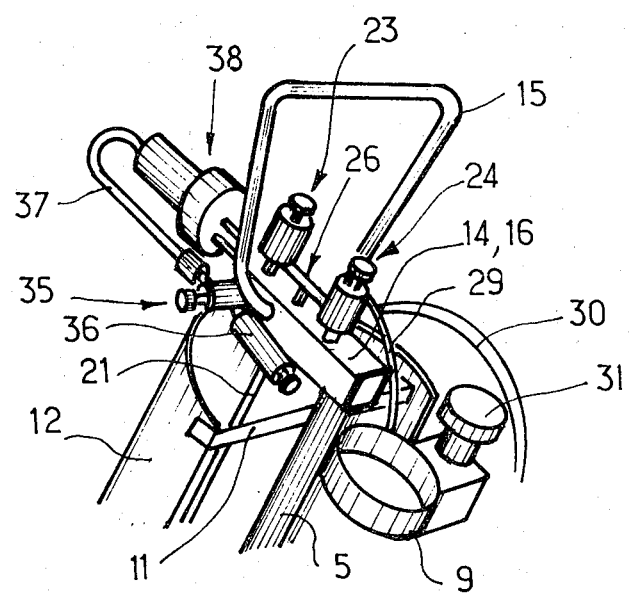

ISOBAROMETRIC AND SELF-CONTAINED APPARATUS FOR SAMPLING PURPOSE ON GASEOUS DRINKS

This invention relates to a constant pressure sampling apparatus for gaseous beverages during fermentation especially in a beer fermentation tank or in a draught beer cask in order to control quality of beer.

During sampling in a fermentation tank of gaseous drinks (for example beer) one must comply with two important rules:

First, it is advisable to take the sample with all the necessary precautions in order to prevent foam formation so that the ratio of carbonic gas in the sample and the volatile elements important for the taste should not be altered. It is also advisable to reduce, as much as possible, the disturbances produced into the tank that is to say the changes of such important parameters as temperature, pressure etc. caused by the sampling in order not to disturb the biological phenomena in their normal activity.

Up to now, the beer sample was taken from the tank by means of a shunt with a coil through a cooled tank.

In spite of the slowing-down caused by the passage through the coil and in spite of the care during measuring, it happened frequently that the bottle contained a sufficient percentage of foam to falsify the measurements.

In order to enable the supply of samples to the laboratory without foam, we used to fill up the bottles completely to an overflowing level in order to cast off the foam. In this respect the foam led to indications of dissolved carbon dioxide and, consequently, its presence signifies a loss of CO2 and constitutes a source of false indications of the amounts of dissolved gas and volatile elements.

Moreover, during filling, the air occluded in the bottle creates a light oxidation of the beer which alters its composition and falsifies the measures which become unrepresentative of the sampled product. For example, the oxidation changes the κ acetolactate into diacethyle being a source of bad taste. This oxidation has a special significance in that one needs precise measures which are given by very expensive analysis material.

The precision of these measures has, of course, no use if the values are changed by the sampling process.

To alleviate the disadvantage of the pressure disturbance and correlatively reducing the foam-formation, someone decided to fill up the sampling bottles through a double cannula with adjusting flow dosing means or to pull out the air in contact with the atmosphere through a calibrated valve (for example for a load of 500 grams approx. 1 lb).

The resulting apparatus effectively allows a considerable reduction of foam formation during the filling up by sampling done at an almost constant pressure.

That apparatus does allow for a light formation of foam when the pressure rises until the load value. During the filling up, the valve opening also creates a small quantity of foam.

Moreover, at the end of the filling, when you take away the apparatus, you suddenly put it in contact with an ambiant atmosphere and therefore create a drastic lowering of pressure that produces the formation of foam.

Although that prior-art system was interesting to some extent for its lowering of the formation of foam, it fails to make full use of the efficiency and precision of the measuring and testing instruments of the laboratory.

The purpose of the invention is to remedy these disadvantages.

The invention proposes sampling methods and apparatus permitting the filling up of the receiving container at a constant pressure under inert gas.

By the use of this apparatus the filling can be entirely foam-free, which considerably reduces loss of carbon dioxide and volatile elements.

According to another feature of this apparatus, the filling up phase, it is preceded by a blowing off by means of nitrogen to avoid any oxidation or air pollution. The sample becomes thus perfectly representative of the contents in the fermantation tank or cask.

Moreover, the sampling method according to the invention does not at all disturb the physical and chemical equilibrium of the beer, nor the normal activity of the microbiological process.

According to an embodiment of the invention, the self-contained constant pressure apparatus for sampling gaseous beverages is made of a tripod and a grip frame. In the frontal section, it contains a support for the sampling container, connected by a tightening mechanism against the dosing member. In the rear, it has two supporting collars for the bottle of inert gas. On the upper part, the distribution head comprises two inlet-taps (one for the gas, the other for the beer), a pressure tap with a blow-off, with a micrometer screw, a gauge for checking the inside pressure and various connections. Between the distribution head and the pressure tap, there is also an element adjusting the flow of the hydraulic connection of delivery commanded by the pressure tap. Connecting components and a pressure reducer are also provided for.

Other characteristics and advantages of embodiment of this invention will appear in the following description made with reference to the annexed drawings FIG. 1 shows a general frontal perspective view of sampling apparatus according to the invention.

FIG. 2 shows a general view of the rear perspective view of the apparatus according to the invention.

FIG. 3 is a side view of the apparatus according to the invention.

FIG. 4 is a detailed perspective view of the upper part of the apparatus according to the invention.

Figure 1:
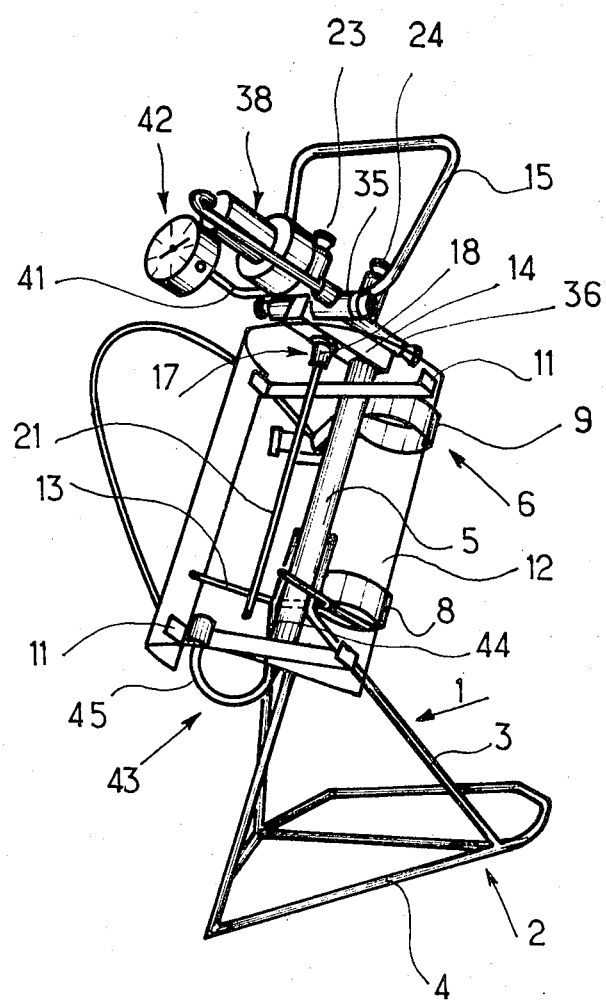
Figure 5:
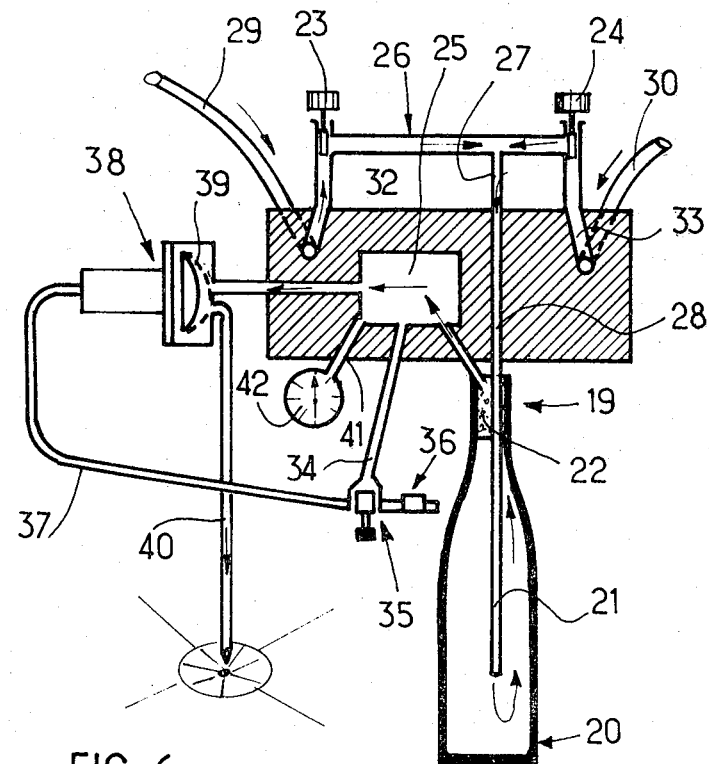
FIG. 5 is a sectional schematic view of the distribution head.
Figure 6:
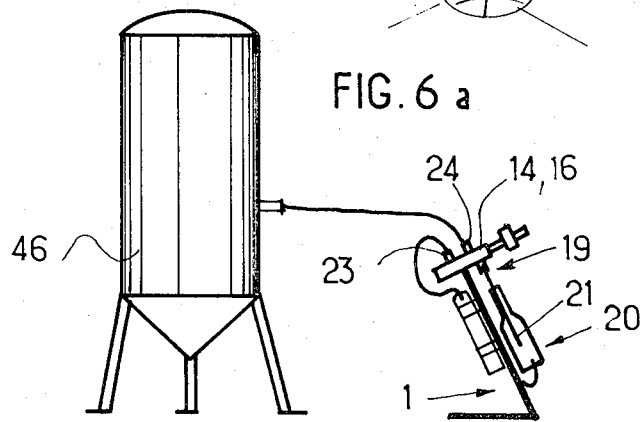
FIG. 6a and 6b are connecting schematic views showing the sampling in a tank or in a cask.
Figure 6:
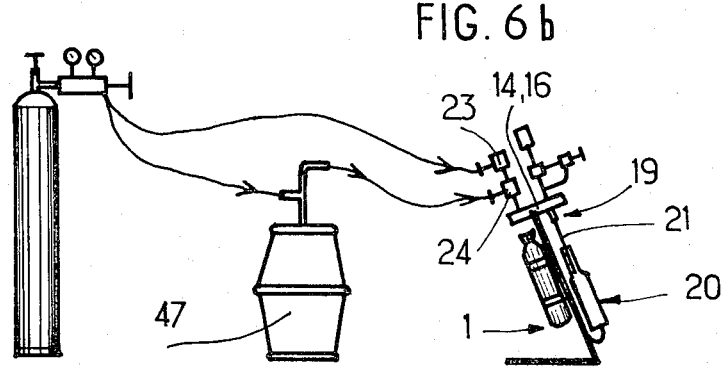

The isobarometric sampling apparatus is first composed of a support frame 1 (made for example of brazed metallic tubes). This frame is made to have a supporting structure 2 in a tripod configuration 3 rigidly secured to a tringular base plate 4, a sloping middle part 5 bearing a support 6 in the rear front, for an inert gas bottle under pressure 7. For example, this support is made of two parallel rings 8 and 9 taking the shape of a collar. The lower ring 8 has a cross bar at 10 against which the bottom of the bottle rests.

All these features give to the apparatus its quality of self-containment.

The middle part 5 bears two flat channel irons 11 locked to the front side, and used as, fixation supports for a convex cover 12 made preferentially of transparent plastic. An additional fork 13 assures protection against shocks. A block 14 is secured to the upper side of the middle part 5.

In a general parallelepipedic configuration, the block 14 provides a mechanical extension between the frame 1 and the grip 15 locked to this block and located at about half-way up from its extremity for favorable center of gravity position.

This block contains the distribution-head 16.

Underneath, the block 14 includes a conic knob 17 with a waterproof-joint 18 which will be used as a closing-cork 19 on the sampling bottle 20. An injection cannula which ends at the lower quarter of the bottle emerges from the central part of the cork.

Additionnaly, the cork has a concentric evacuation hole 22 which allows for the injected gas to escape selectively to a sink or to the atmosphere.

The distribution-head 16 is composed of the upper side of two admission taps 23 and 24 respectively for nitrogen and beer. They regularise the flow-off of nitrogen or beer in a common inside chamber 25 through a T-bridge 26 with a common admission pipe 27 to the sampling container through a separated pipe 28 extended by the cannula 21. Gas and liquid come lateraly into the chamber through the feeding pipes 29 and 30 joined to a pressure reducer. 31 receiving gas from the bottle and beer from the fermentation tank. The inside communication between the gas and liquid inlets and the admission and conrol taps 23 - 24 consists of the different inside pipes 32 and 33.

The distribution-head comprises a lateral exit 34 leading to a tap 35. This tap vents pressure to the two lateral exits. The first exit is in communication with the atmosphere through a blow-off 36 operated by a micrometric screw. The second exit is joined by the pipe 37 to the regulation valve 38 composed of a membrane 39 which controls the evacuation circuit-flow 40 and goes through the common chamber.

The regulation valve 38 closes more or less or totally the evacuation circuit 40 joining the hole 22 to the sink, depending on the pressure given to the membrane 39 by the pipe 37.

The chamber 25 communicates with the manometer 42 by means of a measuring pipe 41.

The injection pipe 28 connected to the admission pipe communicates with the injection cannula 21.

A tightening device 45 lets the neck of the sampling bottle 20 rest against the stopper cork 19.

This tightening device 45 is composed, for example, of a component 44 terminated by a bent rod 45 or extremity which can be removed from and selectively pushed into contact with the bottom of the sampling bottle.

We will now explain the different operating stages of the sampling machine according to the invention.

We put the sampling bottle 20 on its stand and pass the cannula 21 through its neck. We apply the neck to the joint 18 of the closing member 19. Holding the bottle, we lean it strongly against the watertight joint 17 using the tightening device 45, for instance, with the vent rod 45. We clear out the air from the bottle by saturating it with nitrogen under pressure. We do this by turning on the inlet-tap of nitrogen 23. The nitrogen comes into the bottle through the cannula 21 and escapes through the concentric hole 22 of the stop cork.

The clearisng-out of nitrogen to the sink is permited by the valve 38 which is traversable because of the pressure leaving the open tap 35.

When the blow-off ends, we begin the filling up phase. We cut the communication 40 with the sink by actuating the pressure tap 35. The membrane 39 of the valve 38 cuts the link to the sink by the ensuing pressure. Nitrogen is let in till there exists in the sampling bottle a pressure nearing the one of the fermentation tank or of the cask and roughly known by its theorical value given by the pressure gauge 42. The micrometer screw of the terminal blow-off 36 is employed for lowering such pressure.

We cut the arrival of nitrogen to terminate the counterpressure phase and begin the actual filling up phase.

We do this by turning on the tap 24 for the arriving beer. The filling up is slow because of the nitrogen counterpressure which leaves only a small pressure difference. No foam is created. The bottle is filled till it overflows. The overflow of the beer is lead off to the sink by the link 40 through the valve 38 which is open.

We allow for a slow release of gas by setting the atmospheric pressure, using the micrometric screw of the blow-off 36.

The the only steps needed is to disengage the sampling bottle, take it out of the apparatus and to cork it.

Now, the bottle 20 is ready for analysis. Its contents represent the liquid inside the fermentation tank or the cask at high fidelity.

This way, our method is free from the outside disturbances typically caused by sampling and from the disturbances induced in the tank or in the cask by prior-art sampling methods.

The invention allows for sampling in the fermentation tank 46 and also in a beer cask 47 as shown in diagram 6a and 6b.

The invention has been described in detail, allowing of course of some detail modifications or equivalent variations. For instance, the device that applies the bottle against the stop-cork and the regulation valve could be modified.

We claim:

1. A self-contained constant pressure apparatus for sampling gaseous beverages, comprising a frame composed of a tripod and a central inclined stand surmounted by an upper block provided with a handle, with the central stand comprising a first support for a sample drawing recipient (20) and another support for an inert gas bottle (7), and the upper block comprising a distributor-head (16) including two taps (23,24) for admission and regulation of gas and liquid, an exit leading into a tap (35) for pressurising said exit, a regulation valve (38) acting upon distributor-head evacuation means and monitored by the tap (35); the distributor-head at its lower face having an stopper (19) with joint (18) for receiving a neck of the sample drawing recipient; the distributor-head including a common inner chamber (25) for said evacuation means including an evacuation circuit (40), said apparatus including tightening means (43) for applying said neck of the sample drawing recipient against the stopper (19).

2. Apparatus according to claim 1 characterized by the fact that the stopper (19) is perforated at its center by an injection cannula (21) connected to said taps (23, 24) and has a second passage (22) for evacuation.

3. Apparatus according to claim 2 characterized by the fact that the evacuation circuit (40) begins at said second passage (22), goes through the distribution-head (16) by an interior circuit and the common inner chamber (25) and afterwards through the regulating valve (38) to an effluent collector.

4. Apparatus according to claim 1 characterizied by the fact that the tap (35) is connected to a drain (36)

with a micrometric screw allowing for communication with the atmosphere.

5. Apparatus according to claim 1 characterized by the fact that the tightening means (43) are adjustable and terminated by a bent extremity (45), pushable into contact with a bottom of the sample drawing recipient.

6. Apparatus according to claim 1 or 4 characterized by the fact that the tap (35) is connected to the valve (38) by a pipe (37) transmitting operating pressure to the valve (38).

7. Apparatus according to claim 1 characterized by the fact that the valve (38) is a membrane type valve having two outlets connected in said evacuation means and acting according to membrane pressure on said two outlets in order to regulate the flow and the pressure in the evacuation circuit (40).

8. Apparatus according to claim 2 characterized by the fact that the length of the injection cannula (21) is about three quarters of the length of the measurement recipient.

9. Apparatus according to claim 1 characterized by the fact that the common inner chamber (25) leads via a measuring pipe to a pressure unit.

10. Apparatus according to claim 1 characterized by the fact that said other support (6) includes two parallel rings (8) and (9) forming a collar, with one of said rings (8) being lower than the other ring (9) and having a cross bar (10) for supporting a bottom of the gas bottle.

11. Apparatus according to claim 1 characterized by the fact that the sample drawing recipient is protected by a transparent convex cover (12) on said first support.

* * * * *